United States Patent [19]
Birkenstock et al.

[11] Patent Number: 5,410,085
[45] Date of Patent: Apr. 25, 1995

[54] PROCESS FOR THE PREPARATION OF CHLORINE-SUBSTITUTED AROMATIC AMINES AND OF CATALYSTS

[75] Inventors: Udo Birkenstock, Ratingen; Walter Kipshagen, Leverkusen; Herbert Schmidt, Leverkusen; Thomas-Jörn Schulz, Leverkusen; Eberhard Zirngiebl, Köln, all of Germany

[73] Assignee: Bayer Aktiengesellschaft, Leverkusen, Germany

[21] Appl. No.: 139,344

[22] Filed: Oct. 20, 1993

[30] Foreign Application Priority Data

Oct. 27, 1992 [DE] Germany .................. 42 36 203.2

[51] Int. Cl.6 .......................................... C07C 209/36
[52] U.S. Cl. .................................. 564/417; 502/326; 502/339; 564/422; 564/423
[58] Field of Search ............... 564/417, 423; 502/185, 502/339, 326, 325

[56] References Cited

U.S. PATENT DOCUMENTS

| 4,230,637 | 10/1980 | Zander | 260/580 |
|---|---|---|---|
| 5,120,699 | 6/1992 | Weiss et al. | 502/185 |
| 5,120,875 | 6/1992 | Birkenstock | 564/417 |
| 5,236,685 | 8/1993 | Fuchs et al. | 423/387 |

FOREIGN PATENT DOCUMENTS

| 1241664 | 9/1988 | Canada . |
| 0001651 | 6/1979 | European Pat. Off. . |
| 0174563 | 3/1986 | European Pat. Off. . |
| 3928329 | 2/1991 | Germany . |

OTHER PUBLICATIONS

J. S. Taylor & K. M. Lloyd, "Chloracne from 3,3',4,4'-Tetrachloroazoxybenzene...", Perman Series on Environmental Science, vol. 5. pp. 535–544. (Feb. 1982).

Primary Examiner—Allen J. Robinson
Assistant Examiner—Brian M. Burn
Attorney, Agent, or Firm—Sprung Horn Kramer & Woods

[57] ABSTRACT

Chlorine-substituted aromatic amines are prepared by the hydrogenation of chlorine-substituted aromatic nitro compounds in the presence of a catalyst containing platinum and nickel and/or cobalt on an activated charcoal support, the platinum having been simultaneously deposited and reduced on the activated charcoal support in the preparation of the catalyst. Such catalysts are furthermore prepared, as are catalysts containing noble metals on an activated charcoal support, it also being possible for the latter to be used for the reduction of nitronaphthalenes or nitrotoluenes.

10 Claims, 1 Drawing Sheet

PROCESS FOR THE PREPARATION OF CHLORINE-SUBSTITUTED AROMATIC AMINES AND OF CATALYSTS

The present invention relates to an improved process for the preparation of chlorine-substituted aromatic amines by the hydrogenation of chlorine-substituted nitroaromatics in the presence of a noble metal catalyst, and to the preparation of noble metal catalysts.

The hydrogenation of chlorine-substituted aromatic nitro compounds in the presence of noble metal compounds to give the corresponding amines has been known for a long time (see Ullmann, Encyclopädie der technischen Chemie (Encyclopaedia of Chemical Technology), 5th edition, volume A2, page 46 (1985)). A fundamental problem in carrying out this reaction is the undesired dechlorination, which results in a reduced yield of chlorine-substituted aromatic amine. There are a large number of processes which minimise chlorine elimination, e.g. by the use of selectively acting noble metal catalysts such as platinum and ruthenium on support materials (see European patent application A-73 105 and U.S. Pat. No. 4,760,187)

and/or by the use of additives such as ammonia or morpholine (see German Offenlegungsschrift 2,743,610, U.S. Pat. No. 3,145,231 and U.S. Pat. No. 3,361,819) and acid phosphorus compounds (see German Offenlegungsschrift 2,615,079 and U.S. Pat. No. 4,020,107)

and/or by partial catalyst poisoning (see U.S. Pat. No. 4,059,627).

Another possible way of influencing the activity and selectivity of noble metal catalysts is the addition of doping metals such as silver, nickel, copper, lead, bismuth or chromium (see U.S. Pat. No. 3,253,039) and chromium(III) and nickel(II) salts (see U.S. Pat. No. 3,546,297).

If metal doping agents and nitrogen-containing compounds are used simultaneously to suppress the dechlorination reaction, an increase in the formation of 3,3',4,4'-tetrachloroazobenzene (TCAB) and 3,3',4,4'-tetrachloroazoxybenzene (TCAOB) must be expected (see European patent application A-73 105, U.S. Pat. Nos. 4,760,187 and 3,291,032). As TCAB and TCAOB are toxic, the formation of these products is undesirable.

The formation of TCAB and TCAOB can be suppressed by using a catalyst containing platinum and nickel and/or cobalt on an activated charcoal support (see German Offenlegungsschrift 3,928,329).

The catalysts used in the processes described have been obtained by one of the following methods:

Impregnation of the support material with a noble metal salt solution, optionally with subsequent evaporation of the solvent and/or reduction.

Suspension of the support material in an alkaline solution and addition of a noble metal salt solution, noble metal hydroxide precipitating out on the support material, and optionally subsequent reduction.

Addition of bicarbonate to a solution of a noble metal salt in water containing support material in suspension, optionally with subsequent reduction.

Spraying of a noble metal salt solution on to the support material, optionally with subsequent reduction.

The processes and catalysts known hitherto for the preparation of chlorine-substituted aromatic amines are not entirely satisfactory in respect of their selectivity and activity.

A process has now been found for the preparation of chlorine-substituted aromatic amines by the hydrogenation of chlorine-substituted aromatic nitro compounds in the presence of a catalyst containing platinum and nickel and/or cobalt on an activated charcoal support, which is characterised in that the platinum has been simultaneously deposited and reduced on the activated charcoal support in the preparation of the catalyst.

In the process according to the invention, it is possible for example to hydrogenate chlorine-substituted aromatic nitro compounds of formula (I):

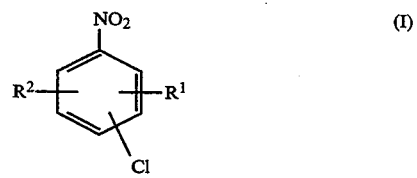

in which $R^1$ and $R^2$ are identical or different and are each hydrogen, methyl or chlorine, to give chlorine-substituted aromatic amines of formula (II):

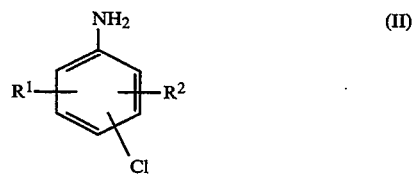

in which $R^1$ and $R^2$ are as defined in formula (I).

Chlorine-substituted aromatic nitro compounds which can be used in the process according to the invention are especially o-, m- and/or p-nitrochlorobenzene, 2,4-, 2,5- and 3,4-dichloronitrobenzene, 2,3,5- and 2,4,6-trichloronitrobenzene and 2-chloro-4-nitrotoluene, and the chlorine-substituted aromatic amines which can accordingly be obtained are especially o-, m- and/or p-aminochlorobenzene, 2,4-, 2,5- and 3,4-dichloroaniline, 2,3,5- and 2,4,6-trichloroaniline and 2-chloro-4-aminotoluene. It is also possible to use any mixtures of chlorinated aromatic nitro compounds to give mixtures of chlorinated aromatic amino compounds.

The process according to the invention can be carried out at temperatures for example in the range 120° to 160° C., preferably 130° to 150° C., and at pressures for example in the range 10 to 200 bar, preferably 80 to 130 bar.

The process according to the invention is preferably carried out in the presence of a solvent, suitable examples being aliphatic alcohols having 1 to 8 C atoms, such as methanol, ethanol, propanol, isopropanol, butanol, isobutanol, pentanol, isopentanol, hexanol and isohexanol, and aromatic hydrocarbons having 6 to 10 C atoms, such as benzene, toluene and xylene. Isopropanol and toluene are preferred.

The process according to the invention is preferably carried out in the presence of a basic compound, particular preference being given here to ammonia, which can be used in gaseous form or as a solution, e.g. a solution in water or one of the above-mentioned solvents. The ammonia can be present in the reaction mixture for example in an amount of 0.2 to 5% by weight, based on the chlorine-substituted aromatic nitro compound used. This amount is preferably 0.3 to 3% by weight, particularly preferably 0.7 to 1.5% by weight. In a continuous procedure, where e.g. solvent, water of reaction, catalyst and/or hydrogen are recycled, any ammonia present is also recycled with these components and can then optionally be brought to a desired content by subsequent proportioning.

The catalyst to be used in the process according to the invention can contain for example 0.3 to 7% by weight, preferably 0.5 to 2% by weight of platinum. It additionally contains nickel and/or cobalt, for example 1 to 100% by weight, preferably 10 to 30% by weight thereof, based on the platinum present. Catalysts containing platinum and nickel are particularly preferred.

The active charcoal support material for the catalyst can consist of porous and/or non-porous activated charcoal. The activated charcoal may be of vegetable or animal origin and may have been activated in any way, for example with steam, zinc sulphate or phosphoric acid. Preferably, at least 80% by weight of the activated charcoal consists of particles with a size of less than 80 $\mu$m. Such activated charcoals are commercially available.

It is an essential feature of the present invention that the platinum has been simultaneously deposited and reduced on the activated charcoal support in the preparation of the catalyst. A possible procedure here consists for example in firstly suspending the activated charcoal support in water to form a slurry, then adding a water-soluble reducing agent, for example hydrazine hydrate, ascorbic acid, formaldehyde or sodium formate, to reduce the platinum, then rendering the mixture alkaline, for example by the addition of sodium hydroxide solution or sodium carbonate, and, finally, slowly adding a platinum salt solution, e.g. an aqueous $H_2PtCl_6$ solution, dropwise. The activated charcoal support, water, water-soluble reducing agent and alkalising agent can also be brought together in a different order.

The water-soluble reducing agent and the alkalising agent can in each case be added e.g. as such or in aqueous solution.

The rate of dropwise addition of the platinum salt solution is controlled so that the platinum is immediately deposited on the activated charcoal support and simultaneously reduced to the metal.

After the reductive deposition of the platinum, nickel and/or cobalt can be added to the mixture for preparation of the catalyst, for example in the form of an aqueous solution of their salts, e.g. the nitrates, chlorides and/or sulphates. In this procedure, nickel and/or cobalt are deposited in the form of their hydroxides.

The reductive deposition of the platinum can be carried out for example at temperatures in the range 0° to 100° C. The preferred operating temperature is 10° to 30° C.

The process according to the invention for the preparation of chlorine-substituted aromatic amines is distinguished by a high selectivity. Only very small proportions of by-products, e.g. TCAB, TCAOB and dehalogenated aromatic amines, are formed. Moreover, the catalyst to be used according to the invention is markedly more active than catalysts known hitherto. This means that a greater amount of chlorine-substituted aromatic amines can be prepared with a given amount of catalyst or that a smaller amount of catalyst than hitherto is required to prepare a particular amount of chlorine-substituted aromatic amines. These advantages are particularly pronounced in the hydrogenation of 3,4-dichloronitrobenzene to 3,4-dichloroaniline.

The present invention further relates to a process for the preparation of catalysts containing noble metals on an activated charcoal support, which is characterised in that the noble metal is simultaneously deposited and reduced on the activated charcoal support. Suitable noble metals are especially palladium and platinum. Other metals or metal compounds, e.g. nickel, copper, lead, bismuth, cobalt, chromium or compounds thereof, can optionally be deposited together with, before or after the noble metal.

Specifically, the process can be carried out as described above for the preparation of a catalyst containing platinum and nickel and/or cobalt.

Such noble metal catalysts can also be used for example for the reduction of nitronaphthalenes or nitrotoluenes.

Unless indicated otherwise, percentages and parts are by weight in the Examples which follow.

EXAMPLES

I. Preparation of Catalysts

Example I-1

An alkaline reducing solution containing 6 parts of sodium hydroxide and 6 parts of hydrazine hydrate in 100 parts of water was added to a suspension of 100 parts of activated charcoal in 600 parts of deionised water. A solution containing 2.5 parts of hexachloroplatinic acid (corresponding to one part of platinum) in 100 parts of water was introduced dropwise into this mixture over 30 minutes and the resulting mixture was then stirred for a further 60 minutes. A solution containing 0.81 part of nickel(II) chloride hexahydrate (corresponding to 0.2 part of nickel) in 100 parts of water was then added and the mixture was stirred for a further 30 minutes. The catalyst suspension was subsequently filtered and the residual catalyst paste was washed with deionised water until the washing water gave a neutral reaction. The catalyst paste prepared in this way (285 parts with a solids content of 35%) contained 1% of platinum and 0.2% of nickel (calculated as metals and based on dry charcoal).

Example I-2 (Comparative Example)

To prepare a catalyst by a known procedure, a solution containing 2.5 parts of hexachloroplatinic acid (corresponding to one part of platinum) in 100 parts of water was introduced dropwise over 30 minutes into a suspension of 100 parts of activated charcoal in 600 parts of deionised water and the mixture was then stirred for a further 60 minutes. An alkaline reducing solution containing 6 parts of sodium hydroxide and 6 parts of hydrazine hydrate in 100 parts of water was then added and the mixture was stirred for a further 60 minutes. A solution containing 0.81 part of nickel(II) chloride hexahydrate (corresponding to 0.2 part of nickel) in 100 parts of water was then added and the mixture was stirred for a further 30 minutes. The catalyst suspension was subsequently filtered and the residual catalyst paste was washed with deionised water until the washing water gave a neutral reaction. The catalyst paste contained 1% of platinum and 0.2% of nickel (calculated as metals and based on dry charcoal).

Example I-3

An alkaline reducing solution containing 6 parts of sodium hydroxide and 6 parts of hydrazine hydrate in 100 parts of water was added to a suspension of 100 parts of activated charcoal in 600 parts of deionised water. A solution containing 2.5 parts of hexachloroplatinic acid (corresponding to one part of platinum) in 100 parts of water was introduced dropwise into this mixture over 30 minutes and the resulting mixture was then stirred for a further 60 minutes. The catalyst suspension was subsequently filtered and the residual catalyst paste was washed with deionised water until the washing water gave a neutral reaction. The catalyst paste prepared in this way (285 parts with a solids content of 35%) contained 1% of platinum, based on dry charcoal.

Example I-4 (Comparative Example)

To prepare a catalyst by a known procedure, a solution containing 2.5 parts of hexachloroplatinic acid (corresponding to one part of platinum) in 100 parts of water was introduced dropwise over 30 minutes into a suspension of 100 parts of activated charcoal in 600 parts of deionised water and the mixture was then stirred for a further 60 minutes. An alkaline reducing solution containing 6 parts of sodium hydroxide and 6 parts of hydrazine hydrate in 100 parts of water was then added and the mixture was stirred for a further 60 minutes. The catalyst suspension was subsequently filtered and the residual catalyst paste was washed with deionised water until the washing water gave a neutral reaction. The catalyst paste contained 1% of platinum, based on dry charcoal.

II. Preparation of Chlorine-substituted Aromatic Compounds

Example II-1

The reference numbers relate to FIG. 1.

BRIEF DESCRIPTION OF THE DRAWINGS

The hydrogenation apparatus used consisted of several tubular reactors (9), (10) and (11) connected in series, which were provided with cooling pipes to dissipate the heat of reaction, the product condenser (12), the separators (13) and (14) and the gas circulating pump (15), which served to produce and maintain a hydrogen circulation.

In a continuous procedure, the chlorine-substituted aromatic nitro compound to be hydrogenated (1), the solvent (2), freshly added catalyst (3) and optionally ammonia (4) were introduced into the kettle (7) via the inlets (1), (2), (3) and (4) and mixed with catalyst (5) recycled in a reaction product/water/solvent mixture.

Figure 1:
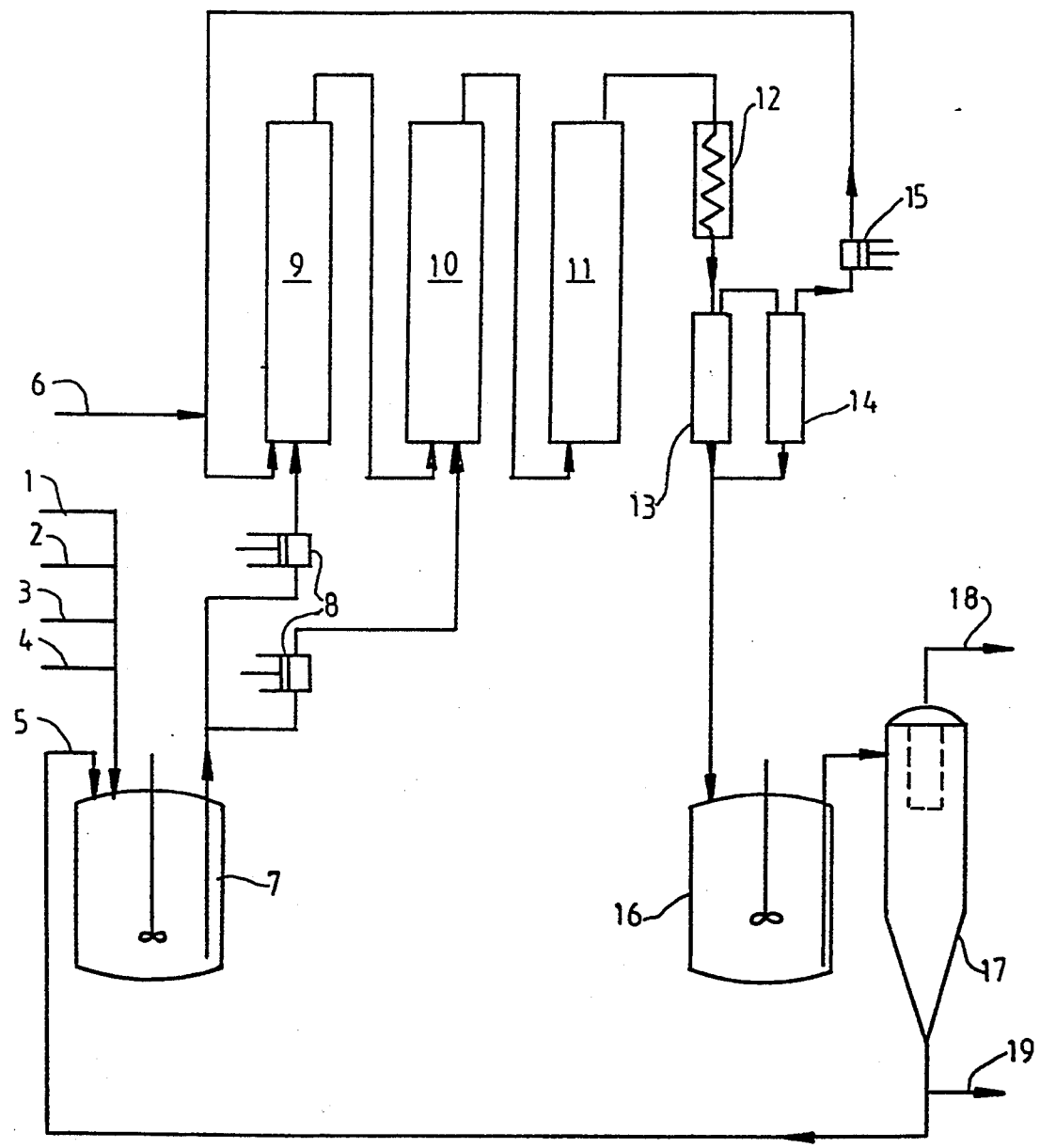

By means of high-pressure pumps (8), the mixture was then fed into the reactors (9) and (10), where it was reacted with hydrogen (6) introduced into the reactor (9) together with recycled hydrogen. The heat of reaction was dissipated with cooling water. The product leaving the reactors was condensed in the condenser (12) and separated from the gas phase in the separators (13) and (14). The gas phase was recycled into the reactor (9) by means of the circulating pump (15). The solution of chlorine-substituted aromatic amine withdrawn from the high-pressure space via the regulating valves was degassed in the kettle (16) and then separated from the catalyst in the filter (17). The solution of chlorine-substituted aromatic amine was then passed on for working-up (18). The catalyst, suspended in a reaction product/water/solvent mixture, was recycled into the next hydrogenation batch via the line (5). Part of this suspension can optionally be withdrawn from the circuit at (19).

2500 kg of 3,4-dichloronitrobenzene, 4200 kg of an isopropanol/water mixture containing 15% of water and 0.35% of ammonia, 0.1 kg of fresh catalyst prepared according to Example I-1 and 2000 kg of finished product solution containing 5% of used catalyst were continuously pumped per hour, as a mixture, into the reactors of the apparatus described above. Thus the circuit permanently contained 1 to 2% of catalyst and 0.1 to 0.2% of ammonia.

The hydrogen pressure was kept at 100 bar and the reaction temperature was adjusted to 140° to 150° C. The product leaving the reactors was free of 3,4-dichloronitrobenzene.

The pH of the resulting solution of 3,4-dichloroaniline was between 9 and 12. The isopropanol/water mixture used as solvent was separated off by distillation and re-used without further working-up. It contained ammonia. Used ammonia was made up to a content of up to 0.35% by weight by the addition of gaseous ammonia to the isopropanol solution. The crude 3,4-dichloroaniline isolated after extensive separation of the water of reaction in a separating bottle contained 99.5% of 3,4-dichloroaniline, less than 20 ppm of TCAB, less than 0.2% of monochloroanilines and less than 0.1% of aniline. The content of TCAOB was less than 0.1 ppm. The product had a melting point of 71.4° to 71.6° C.

The catalyst consumption was reduced by 60% in comparison with the process according to German Offenlegungsschrift 3,928,329.

Example II-2 (Comparative Example)

The procedure was as described in Example II-1 except that the catalyst was replaced with that prepared according to Example I-2.

The crude 3,4-dichloroaniline isolated after extensive separation of the water of reaction in a separating bottle contained 99% of 3,4-dichloroaniline, less than 50 ppm of 3,3',4,4'-tetrachloroazobenzene, less than 0.3% by weight of monochloroanilines, less than 0.3% by weight of aniline and less than 0.1 ppm of 3,3',4,4'-tetrachloroazoxybenzene and had a melting point of 71.5° to 71.6° C.

The catalyst consumption was increased by ca. 130% in comparison with Example II-1.

General remarks on Examples II-3 to II-7

The catalytic activity of various catalysts was determined by a standardised method, where the educt was hydrogenated under pressure in a heatable, stirred, stainless steel autoclave, in each case in the presence of an isopropanol/water mixture and ammonia.

Between 4 and 8 g of catalyst were used for the hydrogenation of 100 g of educt, in each case in 300 g of isopropanol/water mixture (containing 15% of water and 10 ml of 25% aqueous ammonia).

The autoclave was flushed with hydrogen and adjusted to a hydrogen pressure of 100 bar at room temperature. After testing for leaks, the stirrer and heater were switched on simultaneously.

Hydrogen absorption began immediately with a rapid drop in the hydrogen pressure and an increase in the reaction temperature.

Each time the hydrogen pressure dropped to 50 bar, more hydrogen was introduced up to a pressure of 100 bar. Hydrogen absorption had ended after a reaction time of 5 to 6 minutes and a hydrogen uptake of 160 bar. To ensure complete reduction of the nitro compounds, the reaction mixture, heated to 100° C., was stirred for a further 20 minutes at 100° C. under a hydrogen pressure of 100 bar.

The temperature was then lowered to 30° C., with stirring, and the resulting solution of aromatic amines was separated from the catalyst by filtration (run 1).

The catalyst filtered off was re-used for further hydrogenations by the procedure described above (run 2 and subsequent runs).

The filtered amine solution from the first run and the filtered amine solution from the following runs were examined by gas chromatography and/or high performance liquid chromatography for the formation of undesired by-products.

Example II-3

The following were used: 2,4-chloronitrotoluene, 8 g of catalyst prepared according to Example I-3 and 10 ml of 25% aqueous ammonia solution. The catalyst was re-used 7 times (8 runs). After each run, the purity of the 2,4-chlorotoluidine prepared and its content of p-toluidine were determined by gas chromatography. The purity of the 2,4-chlorotoluidine was between 99.2 and 99.4% and the content of p-toluidine was between 0.32 and 0.49%.

Example II-4 (Comparative Example)

The procedure was as in Example II-3 except that catalyst prepared according to Example I-4 was used. The purity of the 2,4-chlorotoluidine was between 98.2 and 99.2% and the content of p-toluidine was between 0.47 and 1.5%.

Example II-5

The procedure was as in Example II-4 except that catalyst obtained according to Example I-1 was used. 6 runs were carried out. The purity of the 2,4-chlorotoluidine was between 99.2 and 99.3% and the content of p-toluidine was between 0.33 and 0.36%.

Example II-6

The following were used: o-nitrochlorobenzene and 4 g of catalyst prepared according to Example I-3. 2 runs were carried out. The purity of the o-chloroaniline obtained was between 98.4 and 99% and the content of aniline was less than 1%.

Example II-7 (Comparative Example)

The procedure was as in Example II-6 except that catalyst prepared according to Example I-4 was used. The purity of the o-chloroaniline obtained was between 96.2 and 97% and the content of aniline was between 2.9 and 3.4%.

Example II-8

The procedure was as described in Example II-3 except that 100 g of 1-nitronaphthalene and 4 g of catalyst prepared according to Example I-1 were used as the educt. The hydrogenation was carried out without the addition of ammonia. The catalyst was recycled once (total of 2 runs). The purity of the 1-naphthylamine obtained was between 99.1 and 99.3%.

Example II-9

The procedure was as described in Example II-3 except that 80 g of a mixture of o- and p-dinitrotoluene and 4 g of catalyst prepared according to Example I-1 were used as the educt. The hydrogenation was carried out without the addition of ammonia. The catalyst was recycled 3 times (total of 4 runs).

The purity of the toluylenediamine obtained was between 99.2 and 99.25% and the content of hexahydro-TDA was between 0.002 and 0.005%.

What is claimed is:

1. A process for the preparation of chlorine-substituted aromatic amines by the hydrogenation of chlorine-substituted aromatic nitro compounds in the presence of a catalyst containing platinum and nickel and/or cobalt on an activated charcoal support, said process further comprising simultaneously depositing and reducing the platinum on the activated charcoal support wherein said depositing and reducing step comprises suspending the activated charcoal support in water to form a slurry, then adding a water soluble reducing agent for reducing the platinum then rendering the mixture alkaline and, finally, slowly adding a platinum salt solution dropwise.

2. The process of claim 1, in which chlorine-substituted aromatic nitro compounds of the formula (I)

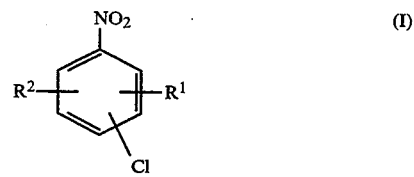

in which
and $R^1$ and $R^2$ are identical or different and are each hydrogen, methyl or chlorine,
are hydrogenated to give chlorine-substituted aromatic amines of the formula (II)

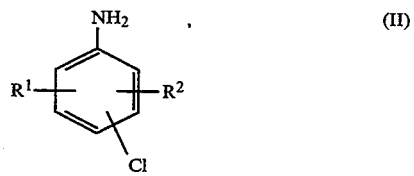

in which
$R^1$ and $R^2$ are defined in formula (I).

3. The process of claim 1, in which the catalyst used contains 0.3 to 7% by weight of platinum and 1 to 100% by weight of nickel and/or cobalt, based on platinum.

4. A process for the preparation of a catalyst containing platinum on an activated charcoal support, comprising suspending the activated charcoal support in water to form a slurry, then adding a water-soluble reducing agent for reducing the platinum, then rendering the mixture alkaline and, finally, slowly adding a platinum salt solution dropwise.

5. The process of claim 4, in which the rate of dropwise addition of the platinum salt solution is controlled so that the platinum is immediately deposited on the activated charcoal support and simultaneously reduced to the metal.

6. The process of claim 4, in which, after the reductive deposition of the platinum, nickel and/or cobalt are added to the mixture for preparation of the catalyst, in the form of an aqueous solution of their salts.

7. The process according to claim 4, in which the reductive deposition of the platinum is carried out at temperatures in the range 0° to 100° C.

8. A process for the preparation of a catalyst containing at least one noble metal on an activated charcoal support, comprising simultaneously depositing and reducing the noble metal on the activated charcoal support, wherein said depositing and reducing step comprises suspending the activated charcoal support in water to form a slurry, then adding a water soluble reducing agent for reducing the platinum then rendering the mixture alkaline and, finally, slowly adding a platinum salt solution dropwise.

9. The process of claim 8, in which, in addition to the noble metal, other metals or metal compounds are also deposited.

10. A method for the reduction of nitronaphthalenes and nitrotoluenes which comprises hydrogenating said compounds in the presence of a catalyst containing at least one noble metal on an activated charcoal support, comprising that the noble metal is simultaneously deposited and reduced on the activated charcoal support wherein said depositing and reducing step comprises suspending the activated charcoal support in water to form a slurry, then adding a water soluble reducing agent for reducing the platinum then rendering the mixture alkaline and, finally, slowly adding a platinum salt solution dropwise.

* * * * *